US009198448B2

(12) United States Patent
Gebreselassie et al.

(10) Patent No.: US 9,198,448 B2
(45) Date of Patent: Dec. 1, 2015

(54) STABLE TOOTH WHITENING GUM WITH REACTIVE INGREDIENTS

(75) Inventors: Petros Gebreselassie, Piscataway, NJ (US); Navroz Boghani, Flanders, NJ (US)

(73) Assignee: Intercontinental Great Brands LLC, East Hanover, NJ (US)

( * ) Notice: Subject to any disclaimer, the term of this patent is extended or adjusted under 35 U.S.C. 154(b) by 1601 days.

(21) Appl. No.: 11/052,672

(22) Filed: Feb. 7, 2005

(65) Prior Publication Data

US 2006/0177383 A1 Aug. 10, 2006

(51) Int. Cl.
*A61Q 11/00* (2006.01)
*A61K 8/22* (2006.01)
*A61K 9/14* (2006.01)
*A61K 9/68* (2006.01)
*A23G 4/06* (2006.01)
*A23G 4/12* (2006.01)
*A23G 4/14* (2006.01)
*A23G 4/20* (2006.01)
*A61K 8/11* (2006.01)
*A61K 8/90* (2006.01)
*A61K 8/97* (2006.01)

(52) U.S. Cl.
CPC *A23G 4/064* (2013.01); *A23G 4/12* (2013.01); *A23G 4/123* (2013.01); *A23G 4/14* (2013.01); *A23G 4/20* (2013.01); *A61K 8/11* (2013.01); *A61K 8/90* (2013.01); *A61K 8/97* (2013.01); *A61Q 11/00* (2013.01); *A23V 2002/00* (2013.01)

(58) Field of Classification Search
USPC .................. 424/53, 48, 49, 401, 472, 496
See application file for complete search history.

(56) References Cited

U.S. PATENT DOCUMENTS

| | | |
|---|---|---|
| 1,633,336 A | 6/1927 | Larson |
| 1,936,456 A | 11/1933 | Larson et al. |
| 2,191,199 A | 2/1940 | Hall |
| 2,197,719 A | 4/1940 | Conner |
| 2,876,167 A | 3/1959 | Manahan |
| 2,886,440 A | 5/1959 | Kramer et al. |
| 2,886,441 A | 5/1959 | Kramer et al. |
| 2,886,442 A | 5/1959 | Kramer et al. |
| 2,886,443 A | 5/1959 | Rosenthal et al. |
| 2,886,444 A | 5/1959 | Rosenthal et al. |
| 2,886,445 A | 5/1959 | Rosenthal et al. |
| 2,886,446 A | 5/1959 | Kramer et al. |
| 2,886,449 A | 5/1959 | Rosenthal et al. |
| 3,004,897 A | 10/1961 | Shore |
| 3,052,552 A | 9/1962 | Koerner et al. |
| 3,117,027 A | 1/1964 | Lindlof et al. |
| 3,124,459 A | 3/1964 | Erwin |
| 3,159,585 A | 12/1964 | Evans et al. |
| 3,241,520 A | 3/1966 | Wurster et al. |
| 3,475,533 A | 10/1969 | Mayrand |
| 3,538,230 A | 11/1970 | Pader et al. |
| 3,664,962 A | 5/1972 | Kelly et al. |
| 3,664,963 A | 5/1972 | Pasin |
| 3,677,771 A | 7/1972 | Kolar, Jr. |
| 3,795,744 A | 3/1974 | Ogawa et al. |
| 3,819,838 A | 6/1974 | Smith et al. |
| 3,821,417 A | 6/1974 | Westall et al. |
| 3,826,847 A | 7/1974 | Ogawa et al. |
| 3,857,964 A | 12/1974 | Yolles |
| 3,862,307 A | 1/1975 | Di Giulio |
| 3,872,021 A | 3/1975 | McKnight |
| 3,878,938 A | 4/1975 | Venables et al. |
| 3,912,817 A | 10/1975 | Sapsowitz |
| 3,930,026 A | 12/1975 | Clark |
| 3,943,258 A | 3/1976 | Bahoshy et al. |
| 3,962,416 A | 6/1976 | Katzen |
| 3,962,463 A | 6/1976 | Witzel |
| 3,974,293 A | 8/1976 | Witzel |
| 3,984,574 A | 10/1976 | Comollo |
| 4,037,000 A | 7/1977 | Burge et al. |
| 4,045,581 A | 8/1977 | Mackay et al. |
| 4,083,995 A | 4/1978 | Mitchell et al. |
| 4,107,360 A | 8/1978 | Schmidgall |
| 4,130,638 A | 12/1978 | Dhabhar et al. |
| 4,136,163 A | 1/1979 | Watson et al. |
| 4,139,639 A | 2/1979 | Bahoshy et al. |
| 4,148,872 A | 4/1979 | Wagenknecht et al. |
| 4,150,112 A | 4/1979 | Wagenknecht et al. |

(Continued)

FOREIGN PATENT DOCUMENTS

| | | |
|---|---|---|
| CA | 1 208 966 | 8/1986 |
| CA | 2 238 925 | 11/1999 |

(Continued)

OTHER PUBLICATIONS

Prencipe et al.; Squeezing out a better toothpaste; Chemtech, Dec. 1995;http://pubs.acs.org/hotartcl/chemtech/95/dec/dec.html; printed Apr. 20, 2004; pp. 1-7.
Gantrez® AN; ISP Polymers for Oral Care; http://www.ispcorp.com/products/oralcare/content/brochure/oral/prod.html, printed Jun. 9, 2004, pp. 1-5.
Demmers et al.; Effect of Surfactants and Proteolytic Enzymes on Artificial Calculus Formation; Surfactants and Enzymes: Calculus; pp. 28-35.
Anonymous; "Caprol 3GO CAS No. 9007-48-1" XP002401201. Retrieved from the Internet: URL: http://www.abiteccorp.com/documents/3go-17_000.pdf.
Anonymous; "HLB Systems" [Online] pp. 1-4, XP002401202. Retrieved from the Internet: URL: http://pharmacal.tripiod.com/ch17.htm.
Ovejero-Lopez et al.; Flavor Release Measurement from Gum Model System; J.Agric. Food Chem.; 2004, vol. 52, pp. 8119-8126.
Rassing, M.R.; Chewing Gum as a Drug Delivery System; Advanced Drug Delivery Reviews, 1994; vol. 13, No. 1-2; pp. 89-121.

*Primary Examiner* — Lezah Roberts
(74) *Attorney, Agent, or Firm* — Hoffmann Baron, LLP

(57) ABSTRACT

Oral compositions including an encapsulated active component(s) are provided. The oral compositions include a carrier composition including a first reactive component. The oral compositions also include an active composition. The active composition includes at least one active component encapsulated in a coating. The coating includes a hydrophilic material and at least one second reactive component, wherein an interaction between the first and second reactive components preserves the activity and/or availability of the active.

15 Claims, No Drawings

(56) References Cited

U.S. PATENT DOCUMENTS

| | | |
|---|---|---|
| 4,156,715 A | 5/1979 | Wagenknecht et al. |
| 4,156,716 A | 5/1979 | Wagenknecht et al. |
| 4,157,385 A | 6/1979 | Wagenknecht et al. |
| 4,159,315 A | 6/1979 | Wagenknecht et al. |
| 4,160,054 A | 7/1979 | Wagenknecht et al. |
| 4,160,820 A | 7/1979 | Wagenknecht et al. |
| 4,187,320 A | 2/1980 | Koch et al. |
| 4,208,431 A | 6/1980 | Friello et al. |
| 4,217,368 A | 8/1980 | Witzel et al. |
| 4,224,345 A | 9/1980 | Tezuka et al. |
| 4,230,688 A | 10/1980 | Rowsell et al. |
| 4,271,199 A | 6/1981 | Cherukuri et al. |
| 4,276,312 A | 6/1981 | Merritt |
| 4,295,845 A | 10/1981 | Sepulveda et al. |
| 4,314,990 A | 2/1982 | Denny, Jr. et al. |
| 4,340,583 A | 7/1982 | Wason |
| 4,352,823 A | 10/1982 | Cherukuri et al. |
| 4,352,825 A | 10/1982 | Cherukuri et al. |
| 4,363,756 A | 12/1982 | Sepulveda et al. |
| 4,367,219 A | 1/1983 | Schole |
| 4,384,004 A | 5/1983 | Cea et al. |
| 4,386,106 A | 5/1983 | Merritt et al. |
| 4,452,821 A | 6/1984 | Gergely |
| 4,457,857 A | 7/1984 | Sepulveda et al. |
| 4,459,425 A | 7/1984 | Amano et al. |
| 4,485,118 A | 11/1984 | Carroll et al. |
| 4,513,012 A | 4/1985 | Carroll et al. |
| 4,515,769 A | 5/1985 | Merritt et al. |
| 4,585,649 A | 4/1986 | Lynch |
| 4,590,075 A | 5/1986 | Wei et al. |
| 4,597,970 A | 7/1986 | Sharma et al. |
| 4,614,649 A | 9/1986 | Gorman et al. |
| 4,614,654 A | 9/1986 | Ream et al. |
| 4,627,987 A | 12/1986 | Barnett et al. |
| 4,634,593 A | 1/1987 | Stroz et al. |
| 4,673,577 A | 6/1987 | Patel |
| 4,711,784 A | 12/1987 | Yang |
| 4,722,845 A | 2/1988 | Cherukuri et al. |
| 4,726,953 A | 2/1988 | Carroll et al. |
| 4,740,376 A | 4/1988 | Yang |
| 4,741,905 A | 5/1988 | Huzinec |
| 4,749,575 A | 6/1988 | Rotman |
| 4,751,095 A | 6/1988 | Karl et al. |
| 4,752,481 A | 6/1988 | Dokuzovic |
| 4,753,790 A | 6/1988 | Silva et al. |
| 4,771,784 A | 9/1988 | Kozin et al. |
| 4,800,087 A | 1/1989 | Mehta |
| 4,804,548 A | 2/1989 | Sharma et al. |
| 4,816,265 A | 3/1989 | Cherukuri et al. |
| 4,822,599 A | 4/1989 | Mitra |
| 4,822,622 A * | 4/1989 | Dokuzovic et al. .............. 426/5 |
| 4,824,681 A | 4/1989 | Schobel et al. |
| 4,828,845 A | 5/1989 | Zamudio-Tena et al. |
| 4,828,857 A | 5/1989 | Sharma et al. |
| 4,842,762 A | 6/1989 | Sabol, Jr. et al. |
| 4,871,570 A | 10/1989 | Barnett et al. |
| 4,904,482 A | 2/1990 | Patel et al. |
| 4,911,934 A | 3/1990 | Yang et al. |
| 4,915,958 A | 4/1990 | Faust et al. |
| 4,918,182 A | 4/1990 | Jackson et al. |
| 4,919,841 A | 4/1990 | Kamel et al. |
| 4,923,684 A | 5/1990 | Ibrahim et al. |
| 4,927,646 A | 5/1990 | Jenner et al. |
| 4,929,447 A | 5/1990 | Yang |
| 4,931,293 A | 6/1990 | Cherukuri et al. |
| 4,933,190 A | 6/1990 | Cherukuri et al. |
| 4,952,407 A | 8/1990 | Record et al. |
| 4,963,369 A * | 10/1990 | Song et al. .............. 426/5 |
| 4,971,797 A | 11/1990 | Cherukuri et al. |
| 4,971,806 A | 11/1990 | Cherukuri |
| 4,978,537 A | 12/1990 | Song |
| 4,981,698 A | 1/1991 | Cherukuri et al. |
| 4,983,380 A * | 1/1991 | Yarborough .............. 424/52 |
| 4,985,236 A | 1/1991 | Ibrahim et al. |
| 4,986,991 A | 1/1991 | Yatka et al. |
| 4,997,659 A | 3/1991 | Yatka et al. |
| 5,004,595 A | 4/1991 | Cherukuri et al. |
| 5,009,900 A | 4/1991 | Levine et al. |
| 5,017,385 A | 5/1991 | Wienecke |
| 5,043,154 A | 8/1991 | Gaffar et al. |
| 5,043,169 A | 8/1991 | Cherukuri et al. |
| 5,057,327 A | 10/1991 | Yatka et al. |
| 5,057,328 A | 10/1991 | Cherukuri et al. |
| 5,059,429 A | 10/1991 | Cherukuri et al. |
| 5,064,658 A | 11/1991 | Cherukuri et al. |
| 5,073,389 A | 12/1991 | Wienecke |
| 5,080,887 A | 1/1992 | Gaffar et al. |
| 5,082,671 A | 1/1992 | Cherukuri |
| 5,084,278 A | 1/1992 | Mehta |
| 5,096,699 A | 3/1992 | Gaffar et al. |
| 5,096,701 A | 3/1992 | White, Jr. et al. |
| 5,100,678 A | 3/1992 | Reed et al. |
| 5,108,763 A | 4/1992 | Chau et al. |
| 5,126,151 A | 6/1992 | Bodor et al. |
| 5,139,793 A | 8/1992 | Johnson et al. |
| 5,139,794 A | 8/1992 | Patel et al. |
| 5,139,798 A | 8/1992 | Yatka et al. |
| 5,154,939 A | 10/1992 | Broderick et al. |
| 5,164,210 A | 11/1992 | Campbell et al. |
| 5,169,657 A | 12/1992 | Yatka et al. |
| 5,169,658 A | 12/1992 | Yatka et al. |
| 5,174,514 A | 12/1992 | Prodi |
| 5,176,900 A | 1/1993 | White, Jr. et al. |
| 5,198,251 A | 3/1993 | Song et al. |
| 5,202,112 A | 4/1993 | Prencipe et al. |
| 5,208,009 A | 5/1993 | Gaffar et al. |
| 5,226,335 A | 7/1993 | Sitte et al. |
| 5,227,182 A | 7/1993 | Song et al. |
| 5,229,148 A | 7/1993 | Copper |
| 5,240,710 A | 8/1993 | Bar-Shalom et al. |
| 5,256,402 A | 10/1993 | Prencipe et al. |
| 5,266,336 A | 11/1993 | McGrew et al. |
| 5,273,741 A | 12/1993 | Gaftar et al. |
| 5,300,283 A | 4/1994 | Prencipe et al. |
| 5,334,375 A | 8/1994 | Nabi et al. |
| 5,334,396 A | 8/1994 | Yatka |
| 5,336,509 A | 8/1994 | McGrew et al. |
| 5,352,439 A | 10/1994 | Norfleet et al. |
| 5,364,627 A | 11/1994 | Song |
| 5,380,530 A | 1/1995 | Hill |
| 5,385,729 A | 1/1995 | Prencipe et al. |
| 5,391,315 A | 2/1995 | Ashkin |
| 5,413,799 A | 5/1995 | Song et al. |
| 5,415,880 A | 5/1995 | Song et al. |
| 5,431,930 A | 7/1995 | Patel et al. |
| 5,437,876 A | 8/1995 | Synosky et al. |
| 5,437,878 A | 8/1995 | Panhorst et al. |
| 5,462,754 A | 10/1995 | Synosky et al. |
| 5,474,787 A | 12/1995 | Grey et al. |
| 5,480,668 A | 1/1996 | Nofre et al. |
| 5,487,902 A | 1/1996 | Andersen et al. |
| 5,498,378 A | 3/1996 | Tsaur et al. |
| 5,501,864 A | 3/1996 | Song et al. |
| 5,503,823 A | 4/1996 | Norfleet et al. |
| 5,505,933 A | 4/1996 | Norfleet et al. |
| 5,523,098 A | 6/1996 | Synosky et al. |
| 5,532,004 A | 7/1996 | Bell et al. |
| 5,582,816 A | 12/1996 | Mandanas et al. |
| 5,589,160 A | 12/1996 | Rice |
| 5,589,194 A | 12/1996 | Tsuei et al. |
| 5,599,527 A | 2/1997 | Hsu et al. |
| 5,603,920 A | 2/1997 | Rice |
| 5,603,971 A | 2/1997 | Porzio et al. |
| 5,618,517 A | 4/1997 | Miskewitz |
| 5,626,892 A | 5/1997 | Kehoe et al. |
| 5,629,035 A | 5/1997 | Miskewitz |
| 5,637,618 A | 6/1997 | Kurtz et al. |
| 5,645,821 A | 7/1997 | Libin |
| 5,645,853 A * | 7/1997 | Winston et al. .............. 424/440 |
| 5,651,958 A | 7/1997 | Rice |
| 5,658,553 A | 8/1997 | Rice |
| 5,676,932 A | 10/1997 | Wason et al. |
| 5,693,334 A | 12/1997 | Miskewitz |
| 5,698,215 A | 12/1997 | Kalili et al. |

(56) References Cited

U.S. PATENT DOCUMENTS

| | | | |
|---|---|---|---|
| 5,702,687 | A | 12/1997 | Miskewitz |
| 5,713,738 | A | 2/1998 | Yarborough |
| 5,716,601 | A | 2/1998 | Rice |
| 5,736,175 | A | 4/1998 | Cea et al. |
| 5,756,074 | A | 5/1998 | Ascione et al. |
| 5,789,002 | A | 8/1998 | Duggan et al. |
| 5,800,848 | A | 9/1998 | Yatka et al. |
| 5,824,291 | A | 10/1998 | Howard |
| 5,869,028 | A | 2/1999 | McGill et al. |
| 5,879,728 | A | 3/1999 | Graff et al. |
| 5,912,007 | A | 6/1999 | Pan et al. |
| 5,939,051 | A | 8/1999 | Santalucia et al. |
| 6,027,746 | A | 2/2000 | Lech |
| 6,056,992 | A | 5/2000 | Lew |
| 6,174,514 | B1 | 1/2001 | Cherukuri et al. |
| 6,190,644 | B1 | 2/2001 | McClanahan et al. |
| 6,239,690 | B1 | 5/2001 | Burbidge et al. |
| 6,261,540 | B1 | 7/2001 | Nelson |
| 6,264,981 | B1 * | 7/2001 | Zhang et al. ............... 424/451 |
| 6,290,933 | B1 | 9/2001 | Durga et al. |
| 6,365,209 | B2 | 4/2002 | Cherukuri |
| 6,379,654 | B1 | 4/2002 | Gebreselassie et al. |
| 6,416,744 | B1 | 7/2002 | Robinson et al. |
| 6,428,827 | B1 | 8/2002 | Song et al. |
| 6,471,945 | B2 | 10/2002 | Luo et al. |
| 6,475,469 | B1 | 11/2002 | Montgomery |
| 6,479,071 | B2 | 11/2002 | Holme et al. |
| 6,485,739 | B2 | 11/2002 | Luo et al. |
| 6,506,366 | B1 | 1/2003 | Leinen et al. |
| 6,534,091 | B1 | 3/2003 | Garces et al. |
| 6,555,145 | B1 | 4/2003 | Cherukuri |
| 6,685,916 | B1 | 2/2004 | Holme et al. |
| 6,692,778 | B2 | 2/2004 | Yatka et al. |
| 6,696,044 | B2 | 2/2004 | Luo et al. |
| 6,759,066 | B2 | 7/2004 | Savage et al. |
| 7,022,314 | B2 | 4/2006 | Barabolak et al. |
| 7,022,352 | B2 | 4/2006 | Castro et al. |
| 7,025,999 | B2 | 4/2006 | Johnson et al. |
| 2001/0043907 | A1 | 11/2001 | Luo et al. |
| 2002/0044968 | A1 | 4/2002 | Van Lengerich |
| 2002/0054859 | A1 | 5/2002 | Alvarez Hernandez |
| 2002/0098157 | A1 * | 7/2002 | Holme et al. .................. 424/49 |
| 2002/0122842 | A1 | 9/2002 | Seielstad et al. |
| 2002/0150616 | A1 | 10/2002 | Vandecruys |
| 2003/0059519 | A1 | 3/2003 | Merkel et al. |
| 2003/0077362 | A1 | 4/2003 | Panhorst et al. |
| 2003/0091721 | A1 | 5/2003 | Ohta et al. |
| 2003/0099740 | A1 | 5/2003 | Colle et al. |
| 2003/0113274 | A1 | 6/2003 | Holme et al. |
| 2004/0037879 | A1 * | 2/2004 | Adusumilli et al. .......... 424/468 |
| 2004/0136928 | A1 | 7/2004 | Holme et al. |
| 2004/0146599 | A1 | 7/2004 | Andersen et al. |
| 2004/0175489 | A1 | 9/2004 | Clark et al. |
| 2004/0238993 | A1 | 12/2004 | Benczedi et al. |
| 2005/0025721 | A1 | 2/2005 | Holme et al. |
| 2005/0112236 | A1 | 5/2005 | Boghani et al. |
| 2005/0214348 | A1 | 9/2005 | Boghani et al. |
| 2005/0220867 | A1 | 10/2005 | Boghani et al. |
| 2005/0260266 | A1 | 11/2005 | Gebreselassie et al. |
| 2006/0034897 | A1 | 2/2006 | Boghani et al. |
| 2006/0193896 | A1 | 8/2006 | Boghani et al. |
| 2006/0263413 | A1 | 11/2006 | Boghani et al. |
| 2006/0263472 | A1 | 11/2006 | Boghani et al. |
| 2006/0263473 | A1 | 11/2006 | Boghani et al. |
| 2006/0263477 | A1 | 11/2006 | Boghani et al. |
| 2006/0263478 | A1 | 11/2006 | Boghani et al. |
| 2006/0263479 | A1 | 11/2006 | Boghani et al. |
| 2006/0263480 | A1 | 11/2006 | Boghani et al. |

FOREIGN PATENT DOCUMENTS

| | | |
|---|---|---|
| CN | 1196235 A | 10/1998 |
| DE | 196 53 100 | 7/1998 |
| EP | 0 067 595 | 12/1982 |
| EP | 0 134 120 | 8/1984 |
| EP | 0 252 374 | 1/1988 |
| EP | 0255260 | 2/1988 |
| EP | 0434321 | 6/1991 |
| EP | 0453397 | 10/1991 |
| EP | 0 608 712 | 8/1994 |
| EP | 0 132 444 | 2/1995 |
| ES | 2 080 703 | 2/1996 |
| ES | 2 190 875 | 8/2003 |
| GB | 875763 | 8/1961 |
| GB | 1255284 | 12/1971 |
| GB | 1444024 | 7/1976 |
| GB | 2 388 581 | 11/2003 |
| JP | 53-136566 | 11/1978 |
| JP | 01206969 | 8/1989 |
| JP | 02-083030 | 3/1990 |
| JP | 02083030 | 3/1990 |
| JP | 02-227044 | 9/1990 |
| RO | 85679 | 11/1984 |
| WO | WO 85/03414 | 8/1985 |
| WO | WO 88/00463 | 1/1988 |
| WO | WO 89/03170 | 4/1989 |
| WO | WO 89/11212 | 11/1989 |
| WO | WO 90/04926 | 5/1990 |
| WO | WO 90/07859 | 7/1990 |
| WO | WO 90/12512 | 11/1990 |
| WO | WO 90/13994 | 11/1990 |
| WO | WO 91/07104 | 5/1991 |
| WO | WO 92/02145 | 2/1992 |
| WO | WO 92/06160 | 4/1992 |
| WO | WO 95/33034 | 12/1995 |
| WO | WO 96/08166 | 3/1996 |
| WO | WO 96/19193 | 6/1996 |
| WO | WO 97/02009 | 1/1997 |
| WO | WO 97/02011 | 1/1997 |
| WO | WO 98/03076 | 1/1998 |
| WO | WO 98/15192 | 4/1998 |
| WO | WO 98/18339 | 5/1998 |
| WO | WO 98/23165 | 6/1998 |
| WO | WO 93/29088 | 7/1998 |
| WO | WO 99/15032 | 4/1999 |
| WO | WO 99/27798 | 6/1999 |
| WO | WO 99/43294 | 9/1999 |
| WO | WO 99/43924 | 9/1999 |
| WO | WO 99/62354 | 12/1999 |
| WO | WO 00/01253 | 1/2000 |
| WO | WO 00/35296 | 6/2000 |
| WO | WO 00/35298 | 6/2000 |
| WO | WO 00/35398 | 6/2000 |
| WO | WO 00/36924 | 6/2000 |
| WO | WO 00/69282 | 11/2000 |
| WO | WO 00/75274 | 12/2000 |
| WO | WO 01/76384 | 10/2001 |
| WO | WO 02/47489 | 6/2002 |
| WO | WO 02/055649 | 7/2002 |
| WO | WO 02/076231 | 10/2002 |
| WO | WO 02/000039 | 11/2002 |
| WO | WO 02/102362 | 12/2002 |
| WO | WO 03/020047 | 3/2003 |
| WO | WO 03/039503 | 5/2003 |
| WO | WO 03/063604 | 8/2003 |
| WO | WO 2004/006967 | 1/2004 |
| WO | 2004043388 A2 | 5/2004 |
| WO | WO 2004/077956 | 9/2004 |
| WO | WO 2005/013712 | 2/2005 |
| WO | WO 2005/016022 | 2/2005 |
| WO | WO 2005/051427 A1 | 6/2005 |
| WO | WO 2005/079598 | 9/2005 |
| WO | WO 2005/087020 | 9/2005 |
| WO | WO 2005/091918 | 10/2005 |
| WO | WO 2006/003349 | 1/2006 |
| WO | WO 2006/079056 | 7/2006 |
| WO | WO 2006/086061 | 8/2006 |

* cited by examiner

STABLE TOOTH WHITENING GUM WITH REACTIVE INGREDIENTS

FIELD

The present invention is generally directed to oral compositions containing an encapsulated active ingredient. In particular, the invention is directed to oral compositions including an active ingredient encapsulated within a reactive barrier coating for substantially preventing a stability-limiting ingredient in the composition from reacting with the active.

BACKGROUND

Unblemished white teeth have long been considered cosmetically desirable. Unfortunately, in the absence of thorough dental cleaning, teeth can become discolored or stained from color-causing substances present in food, beverages, tobacco, and the like, and internal sources such as blood, amalgam-based fillings, and antibiotics (e.g., tetracycline).

Currently, there are a number of methods for removing stains in teeth. These methods are generally based on the use of abrasives, hydrolytic agents or oxidizing agents to break down the staining material. For example, mechanical methods of tooth cleaning are known whereby the stain is mechanically abraded through the use of abrasives or polishing agents normally employed in toothpaste preparations. Typical preparations containing abrasives are toothpastes, gels or powder dentifrices, which require close contact with the teeth. Brushing and similar scrubbing or polishing action is typically required as a compliment to successful stain removal. Typical abrasives include hydrated silica, calcium carbonate, sodium bicarbonate and alumina.

Hydrolytic agents including proteolytic enzymes can also be used to whiten teeth. These products are usually in the form of pastes or gels, and function to whiten teeth by removing the plaque and calculus that have entrapped the stain.

Oxidizing agents such as urea peroxide, hydrogen peroxide or calcium peroxide, represent the most common forms of whitening agents for tooth enamels. It is believed that peroxides whiten teeth by releasing hydroxyl radicals capable of breaking down the plaque/stain complex into a form that can be flushed away or removed by an abrasive.

Other active stain-removing components include surface-active agents, such as anionic surfactants and chelators, which have been incorporated into stain-removing compositions because of their stain-removing properties. For example, anionic surfactants typically employed in dentifrice compositions include sodium lauryl sulfate and sodium N-lauryl sarcosinate. Furthermore, chelators, such as polyphosphates, are typically employed in dentifrice compositions as tartar control ingredients. For example, tetrasodium pyrophosphate and sodium tri-polyphosphate are typical ingredients found in such compositions.

Stain-removing gum compositions are known. For example, gum compositions including sodium tripolyphosphate and xylitol are known. Also, gum compositions are known, which include hexametaphosphate and an abrasive silica material. Moreover, a dental gum is known, which includes the following ingredients: sodium tripolyphosphate, tetrasodium pyrophosphate, a silica abrasive and zinc acetate. A whitening gum composition is also known, which includes the abrasives sodium bicarbonate and calcium carbonate, and is sold under the brand name V6®.

Moreover, stain-removing gum compositions are known that include anionic surfactants such as fatty acid salts. For example, sodium stearate is a fatty acid salt employed in a gum product sold under the brand name Trident White® (see U.S. Pat. Nos. 6,471,945, 6,479,071 and 6,696,044). Furthermore, copending, commonly-owned U.S. patent application Ser. No. 10/901,511 discloses stain-removing gum compositions containing a salt of ricinoleic acid.

Unlike toothpaste, mouthwash and other dentifrice compositions, tooth whitening gum compositions present unique problems. For example, certain tooth whitening active ingredients can react adversely with other ingredients in gums. This results in short shelf-life, as well as the production of undesirable by-products. For example, certain anionic surfactants interact with lecithin, which is often used in gums and other food products to help different parts mix together well. Moreover, phosphate salts, such as polyphosphates, and certain anionic surfactants undergo changes in acidic formulations, such as fruit gums.

In view of the foregoing, it would be beneficial to provide further gum compositions for cleaning teeth. In particular, it would be beneficial to provide a tooth whitening gum where the stain-removing active agent was encapsulated within a barrier coating that substantially prevents the active agent from reacting with other gum ingredients.

SUMMARY OF THE INVENTION

The present invention is generally directed to oral compositions in which an active ingredient has been effectively incorporated therein so that the reaction between a stability-limiting ingredient in the composition and the active ingredient is limited. In so doing, the oral composition is stabilized, shelf-life is increased and the active remains available for its intended purpose.

In one aspect of the present invention, there is provided an oral composition including a carrier composition and an active composition. The carrier composition may include a first reactive component, which is also referred to as the stability limiting component. If the first reactive component is exposed to the active composition in absence of the reactive barrier coating described below, the first reactive component may react with the active resulting in less active being available for its intended use.

The active composition includes at least one active component encapsulated in a coating, which is also referred to as the reactive barrier coating. The reactive barrier coating may include a hydrophilic material; and a second reactive component. An interaction between the first and second reactive components preserves the activity and/or availability of the active.

In the present specification, the terms "first reactive component" and "stability-limiting component" may be used interchangeably. The first reactive component may react unfavorably with the active component.

The term "second reactive component" may be used interchangeably with the terms "reactive barrier agent", "reactive barrier component" and the like. The second reactive component assists in preventing any undesirable reaction or interaction between the first reactive component and the active.

The phrase "preserve the activity and/or availability of the active" when used in the present invention includes protecting the active component such that it will maintain its activity, or at least any substantial loss of activity and/or degradation of the active will be reduced during manufacture and storage over a given time period, as compared to similar compositions not practicing the present invention. The phrase includes maintaining the active chemically or physically intact for a given time period as discussed herein. In particular, through the interaction of the first and second reactive components in the oral composition, less of the first reactive component (i.e., the stability-limiting component) is capable of interacting with the active component. As a result, there is a reduction in the extent and/or rate of degradation of the active component by the first reactive component. For example, in some embodiments where the active is a chelating agent, such as a polyphosphate, the polyphosphate is coated with a reactive barrier coating, which includes a buffer. The buffer is the second reactive component, which interacts with a first reactive component, such as a food acid. As a result of the reaction between the buffer (second reactive component) and the food acid (first reactive component), the polyphosphate active is chemically and physically "protected". That is to say, its activity is maintained or any loss of its activity is reduced than would otherwise be possible.

The reactive barrier coating extends the stability of the oral composition, as compared to the same composition in the absence of the coating. In particular, the coating provides a physical and chemical barrier between the active and a stability-limiting component in the oral composition.

The oral compositions of this invention can include, but are not limited to, any number of compositions, including gums, confectionary compositions, toothpastes and mouthwashes. For example, certain aspects of the present invention relate to tooth whitening gum compositions.

In some embodiments, the tooth whitening gum composition may include a gum base and an active composition. The gum base includes at least one first reactive component, which upon exposure to one or more active components, reacts therewith to reduce the activity of the active. The active composition includes at least one active component encapsulated in a reactive barrier coating. The reactive barrier coating includes a hydrophilic material; and a second reactive component, which interacts with the first reactive component to preserve the activity and/or availability of the active.

Other aspects of the present invention relate to methods for preparing and using the inventive oral compositions herein.

In some embodiments, the invention provides a method for removing stains from teeth. This method includes providing an oral composition including a carrier composition and an active composition. The carrier composition includes at lease one first reactive component. The active composition includes at least one active component encapsulated in a reactive barrier coating. The reactive barrier coating includes a hydrophilic material; and at least one second reactive component, wherein an interaction of the first and second reactive components preserves the activity and/or availability of the active. The method further includes contacting the teeth with the provided oral composition for a sufficient time to remove stains from the teeth. For example, in one embodiment, stains may be removed from teeth by chewing an effective amount of a stain-removing gum composition provided herein.

Gum compositions provided herein can be prepared in any number of ways. For example, the active component can be coated with a water-soluble hydrophilic material and the reactive barrier agent, and then combined with a gum base, or with a coating for the gum, or with both.

In some embodiments, the present invention provides a method of preparing a tooth whitening gum composition that includes: encapsulating a tooth whitening active component in a reactive barrier coating. The reactive barrier coating includes a hydrophilic material; and a component reactive with a stability-limiting component in the gum composition. The method also includes heating a gum base to soften the base; mixing the softened gum base with the encapsulated tooth whitening active component to obtain a substantially homogeneous mixture; cooling the mixture; and forming the cooled mixture into individual gum pieces. Other components, such as including, but not limited to, sweeteners, flavorants, fillers and colorants may also be included in the gum base.

In further embodiments, the present invention provides a method of preparing a tooth whitening gum composition that may include suspending tooth whitening active particles in a fluidized air stream; and spraying a reactive barrier coating onto the suspended active particles, wherein the coating includes a hydrophilic material and a component reactive with a stability-limiting component in the gum composition.

DETAILED DESCRIPTION OF THE INVENTION

As used herein the transitional term "comprising," (also "comprises," etc.) which is synonymous with "including," "containing," or "characterized by," is inclusive or open-ended and does not exclude additional, unrecited elements or method steps, regardless of its use in the preamble or the body of a claim.

As used herein, the term "gum compositions" is intended to include any gum compositions, including "chewing gum" and "bubble gum."

As used herein, the term "active component" refers to any encapsulated material included in the oral compositions of the present invention, wherein the active provides some desirable property upon release from encapsulation (for example, when the encapsulated material has been subjected to mastication). Examples of suitable actives include tooth whitening agents, such as surfactants, chelating agents, hydrolytic agents, oxidizing agents and high intensity sweeteners. Other examples of suitable actives include flavors, medicaments, vitamins, etc.

The term "fatty acid salt" is a compound formed by replacing hydrogen in a fatty acid by a metal (or a radical that acts like a metal).

The term "phosphate salt" is meant to encompass pyrophosphates, triphosphates, polyphosphates, polyphosphonates and combinations thereof.

The present invention is directed to compositions with stain-removing properties for producing a whitening effect on dental surfaces that are treated with the same. Such compositions are especially suitable for removing stains, which adhere to, or are entrapped in materials on, the surface of teeth and for preventing build-up of the stain entrapping material and stains on dental surfaces. The compositions of the present invention are retained in the oral cavity for a sufficient time to contact the dental surfaces for purposes of providing beneficial dental effects.

The compositions of the present invention may be in a form selected from, for example, dentifrices including mouthwashes, mouth rinses, toothpastes, tooth powders, tooth hardeners, antiplaque compositions, dental creams, dental flosses, liquids, gels, and the like; chewing gums, including center-filled gums, and the like; and confectionaries, including mints, lozenges, and the like. In some embodiments, the compositions of the present invention are in the form of chewing gums.

In accordance with the present invention, a stain-removing effective amount of a an encapsulated tooth whitening active is employed in the compositions of the present invention to provide effective stain-removing activity. For example, the encapsulated tooth whitening active may be one or more of the following: chelating agents, such as phosphate salts, surfactants, such as fatty acid salts, hydrolytic agents, such as proteolytic enzymes, and oxidizing agents, such as peroxides. Such agents facilitate the effective removal of dental stains.

Tooth whitening agents can substantially interact with other ingredients in oral compositions. This results in short shelf-life, as well as the production of undesirable by-products. The present invention is directed to overcoming this problem.

For example, by encapsulating the active within a reactive barrier coating, the physical and chemical interaction between a stability-limiting component in the oral composition and the active is substantially reduced. Thereby, the oral composition is stabilized. The reactive barrier coating includes a water-soluble hydrophilic material that provides a physical barrier between the active ingredient and the stability-limiting ingredient. In some embodiments, the water-soluble hydrophilic material is selected from at least one of the following: gum arabic, starch, gelatin, alginates, alkyl and hydroxycellulose, carrageenen, microcrystalline cellulose, gum agar, hydroxyethylcellulose, poly(acrylic acid), polyethylene glycol, polyvinyl alcohol, polyvinylpyrrolidone, modified starch, xanthan gum, zein, polyols, and guar gum.

In addition to providing a physical barrier between the active ingredient and the stability-limiting component, the barrier coating further provides a chemical barrier between these components. In particular, the reactive barrier coating includes a reactive agent that reacts with a stability-limiting component in the composition so as to chemically neutralize its effect on the active. This prevents premature degradation of the active and stabilizes the oral composition. Applicants have discovered that encapsulating the tooth whitening active component in the reactive barrier coating increases the shelf-life of the oral composition and avoids the production of undesirable by-products.

In some embodiments, the interaction of the first and second reactive components lessens the capability of the first reactive component to interact with the at least one active component. In further embodiments, the degradation of at least one active component, over time, is lessened due to the interaction of the first and second reactive components, as compared to the composition without the interaction.

In other embodiments, this interaction of the first and second reactive components increases the shelf-life of the oral composition as measured by the presence of higher active component amounts, as compared to the composition without the interaction. In still other embodiments, the interaction of the first and second reactive components provides a shelf-life of at least about one year, as measured by the presence of at least 75% of the active remaining. In yet still other embodiments, the interaction of the first and second reactive components provides a shelf-life of at least about six months, as measured by the presence of at least 90% of the active remaining.

Chelating agents are one group of encapsulated tooth whitening agents suitable for use in the compositions of the present invention. Chelators are capable of strongly binding with metal ions, such as calcium. For example, chelating agents are able to complex calcium found in the cell walls of bacteria, a major component of plaque. Chelating agents can also disrupt plaque by removing calcium from the calcium bridges, which help hold the plaque matrix together.

Examples of suitable chelators include phosphate salts. In some embodiments, the phosphate salt is selected from one of the following: pyrophosphates, triphosphates, polyphosphates, polyphosphonates and combinations thereof.

As shown in Table 1 below, polyphosphates, such as sodium tripolyphosphate (STP) and sodium hexametaphosphate (SHMP), which are commonly employed in tooth whitening gum compositions, react with stability-limiting acids (e.g., citric acid). This reduces the shelf-life of the oral composition and results in the production of undesirable by-products. By encapsulating the polyphosphate active in a barrier coating, the adverse effects of the acid on the polyphosphate are reduced. In some embodiments, the barrier coating for the polyphosphate includes one of the following hydrophilic materials: gum arabic, starch or gelatin. The barrier coating for the polyphosphate may also include a phosphate buffer as a reactive agent. The phosphate buffer, when in the presence of a stability-limiting acid, reacts therewith to stabilize the oral composition.

TABLE I

| | Actives | Reactive barrier coating system | | Stability limiting components |
|---|---|---|---|---|
| | | Physical barrier | Reactive Chemical barrier | |
| 1 | Polyphosphates: STP SHMP | Gum Arabic, starch, gelatin | Phosphate buffer | Acids |
| 2 | Enzymes: Protease: papaine Lipase Amylase Glucoamylase | Gum Arabic, starch, gelatin | Phosphate buffer Citrate buffer Silica Reducing agents | Flavors, Peroxides Florides Water |
| 3 | Oxidizing agents: Peroxides | Gum Arabic Starch Guar gum | Silica Citrate buffer | Flavors, aldehydes |
| 4 | Intense Sweeteners: Neotame Aspartame | Gum Arabic Starch Guar gum | Citrate buffer | Flavors Aldehydes Glycerin |
| 5 | Surfactants: Fatty Acid Salts | Gum Arabic Starch Gelatin | Citrate buffer Phosphate buffer | Acids Lecithin |

Encapsulating sodium tripolyphosphate (STP) increases its stability in acidic gum as compared to free STP. The result is an increase in the shelf-life of the gum, and a reduction in the production of undesirable by-products.

Hydrolytic agents are another group of encapsulated tooth whitening agents suitable for use in the oral compositions of the present invention. Hydrolytic agents function to whiten teeth by removing the plaque and calculus that entrap the stain. Referring to Table 1 above, examples of hydrolytic agents which may be employed in the oral compositions of the present invention include proteolytic enzymes (e.g., papaine), lipase, amylase and glucoamylase. Such hydrolytic agents react unfavorably with the following stability-limiting components: flavors, peroxides, florides and water. By coating the enzyme with a material such as gum arabic, starch or gelatin, a physical barrier against these stability-limiting components is provided. Preferably, the barrier coating for the enzyme further includes one of the following reactive barrier agents: phosphate buffer, citrate buffer, silica or reducing agents. These reactive agents, when in the presence of stability-limiting flavors, peroxides, florides or water, react therewith to stabilize the oral composition.

With further reference to Table 1, oxidizing agents, such as peroxides, are another group of encapsulated tooth whitening agents suitable for use in the oral compositions of the present invention. Peroxides are believed to whiten teeth by releasing hydroxyl radicals capable of breaking down the plaque-stain complex into a form that can be flushed away or removed by abrasives. Encapsulating peroxides in a material such as gum arabic, starch or guar gum substantially physically prevents peroxides from interacting with stability-limiting flavors or aldehydes, which are often present in oral compositions. The reactive agent in the coating provides the chemical barrier between the active and the stability-limiting component. In some embodiments, the reactive agent in the barrier coating for the peroxide is silica or a buffer, such as citrate buffer, which in the presence of stability-limiting flavors or aldehydes, react therewith to stabilize the oral composition.

Surfactants, such as anionic surfactants, are yet another example of a group of encapsulated tooth whitening agents suitable for use in the inventive compositions. Certain fatty acid salts interact with lecithin, which is often used in gums and other food products to help different parts mix together well. Moreover, fatty acid salts can undergo changes in acidic formulations, such as fruit gums. By encapsulating surfactants in a physical barrier coating of a water-soluble hydrophilic material, such as gum arabic, starch or gelatin, these adverse interactions are substantially reduced. Preferably, a chemical barrier is also provided. For example, in some embodiments, the barrier coating for the surfactant includes a buffer, such as a citrate buffer, which can neutralize the effect of a stability-limiting acid. Alternatively, the barrier coating for the surfactant may include a phosphate buffer, which can react/interact with lecithin, thereby reducing any interaction between lecithin and the surfactant active.

Intense sweeteners, such as Neotame and Aspartame, are other examples of suitable encapsulated active agents suitable for use in the inventive compositions. In particular, it is common to employ such sugar substitutes in tooth whitening gum compositions. As shown in Table 1, encapsulating intense sweeteners in a material such as gum arabic, starch or guar gum substantially prevents these actives from physically interacting with stability-limiting flavors, aldehydes or glycerin which are often present in oral compositions. The barrier coating for the sweetener may further include a buffer, such as a citrate buffer. A citrate buffer, when in the presence of flavors, aldehydes or glycerin, reacts therewith to further stabilize the oral composition.

The term "stain-removing effective amount" as used herein is an amount of stain-removing agent(s) disclosed herein that is sufficient to prevent, eliminate, or at least reduce, the presence of stains on dental surfaces in warm-blooded animals including humans, but low enough to avoid any undesirable side effects. This stain-removing effective amount of stain-removing agent(s) may vary with the type and extent of the particular stain, the age and physical condition of the warm-blooded animal, including humans being treated, the duration of treatment, the nature of concurrent therapy, the specific stain-removing agent employed, and the particular carrier from which the stain-removing agent is applied.

The concentration of the stain-removing agents in the composition of the present invention depends on the type of composition (e.g., toothpaste, mouthwash and rinse, lozenge, chewing gum, confectionary, and the like) used to apply the stain-removing agents to the dental surfaces, due to the differences in the efficiency of the compositions contacting the teeth and due also to the effective amount of the composition generally used. The concentration may also depend on the levels of the stains present.

Except as otherwise noted, the amount of the components incorporated into the compositions according to the present invention is designated as percentage by weight based on the total weight of the composition.

As described above, an oral composition of the present invention can be a gum composition, such as chewing gum composition. The chewing gum compositions of the present invention may be coated or uncoated, and be in the form of slabs, sticks, pellets, balls and the like. The composition of the different forms of the chewing gum compositions will be similar but may vary with regard to the ratio of the components. For example, coated gum compositions may contain a lower percentage of softeners. Pellets and balls may have a chewing gum core, which has been coated with either a sugar solution or a sugarless solution to create the hard shell. Slabs and sticks are usually formulated to be softer in texture than the chewing gum core.

Center-filled gum is another common gum form. The gum portion has a similar composition and mode of manufacture to that described above. However, the center-fill is typically an aqueous liquid or gel, which is injected into the center of the gum during processing. The tooth whitening agent(s) could optionally be incorporated into the center-fill during manufacture of the fill, incorporated directly into the chewing gum portion of the total gum composition, or both. The center-filled gum may also be optionally coated and may be prepared in various forms, such as in the form of a lollipop.

In some embodiments of the present invention, a coated gum may be formed, wherein the tooth whitening agent(s) is in at least one of the core or the gum coating. For example, an abrasive agent may be incorporated into the coating, and surface actives (e.g., surfactant and/or chelating agent) may be incorporated into the gum base. By providing the abrasive in the coating, the stain is first mechanically abraded by the abrasive in combination with chewing, which requires close contact with the teeth. In particular, the abrasive tends to have a short time before it goes into solution. Whereas the abrasive continues to have a chemical effect in removing the stain after it is released from the coating into the saliva, it may be advantageous to enhance the mechanical abrasion initially by providing it in the coating layer. Furthermore, the coating provides another effective vehicle for delivering a surface-active.

It is also well within the contemplation of the present invention that the tooth whitening agent(s) can be incorporated into the gum base. The gum base provides another effective vehicle for delivering the tooth whitening agent(s), such as abrasives and surface-active agents because it permits protracted contact of the tooth whitening agents with the teeth. For example, the tooth whitening agent(s) can chemically remove the stain once released from the gum base and/or gum coating into saliva.

Chewing gum compositions of the present invention may include a gum base and most of the other typical chewing composition components, such as sweeteners, softeners, flavorants and the like. At least one encapsulated tooth whitening active is employed in some embodiments of the gum compositions.

The gum compositions of some embodiments have an increased "shelf-life" as a result of the incorporation of the second reactive component. The second reactive component reacts with the stability limiting component, thereby reducing the stability limiting component's effect on the active. For example, at least about 90% of the active remains at about six months in the compositions, and at least about 75% of the active remains at about one year of shelf-life.

Surfactants

The oral compositions of the present invention include encapsulated tooth whitening agent(s) as provided herein. For example, the composition may include anionic surfactants and nonionic surfactants or mixtures thereof. Anionic surfactants useful herein include medium and long chain fatty acid esters and salts. In some embodiments, the anionic surfactant is a water-soluble salt of a fatty acid having from 14 to 25 carbon atoms. The salt may include a metal ion that can be a divalent metal ion or a monovalent metal ion. For example, the metal ion can be selected from sodium, potassium, calcium, magnesium and combinations thereof.

Suitable examples of fatty acid salts include salts of stearate and palmitrate. Other examples include hydroxy fatty acid salts, such as salts of ricinoleic acid, castor oil and ergot oil. Ricinoleic acid accounts for about 90% of the triglyceride fatty acids of castor oil, and up to about 40% of the glyceride fatty acids of ergot oil. Other suitable hydroxy fatty acid salts include, but are not limited to, those derived from the following: lesquerolic acid, densipolic acid, auricolic acid and β-dimorphecolic acid. Combinations of hydroxy fatty acid salts may also be employed.

The water-soluble salts of hydroxy fatty acids may be derived from naturally occurring fatty acids having at least one hydroxyl functionality, such as ricinoleic acid. Furthermore, the surfactants employed in the present invention or the fatty acids from which they are derived may be chemically or enzymatically modified so as to contain at least one hydroxyl functionality.

The fatty acid salts may be derived from fatty acids found, for example, in animals, plants or bacteria. The polar —COOH group on short-chain fatty acids (e.g., 2-4 carbon atoms) and even medium-chain (e.g., 6 to 10 carbon atoms) is typically enough to make them soluble in water. However, as chain length increases (e.g., from 14 to 25 carbons), the fatty acid type becomes progressively less water soluble and tends to take on oily or fatty characteristics. The presence of a hydroxy group on long-chain fatty acids increases water solubility. Therefore, Applicants have found that water-soluble salts of hydroxy fatty acids having from 14 to 25 carbon atoms are useful in the compositions of the present invention. In particular, the water solubility of a hydroxy fatty acid salt allows it to solubilize an established stain into the saliva and loosens it so that it can be easily removed by chewing, brushing or saliva.

In some embodiments, the inventive oral compositions can include other anionic or nonionic surfactants. For example, other suitable surfactants may include the following anionic or non-ionic surfactants: sulfated butyl oleate, sodium oleate, salts of fumaric acid, potassium glomate, organic acid esters of mono- and diglycerides, stearyl monoglyceridyl citrate, succistearin, dioctyl sodium sulfosuccinate, glycerol tristearate, lecithin, hydroxylated lecithin, sodium lauryl sulfate, acetylated monoglycerides, succinylated monoglycerides, monoglyceride citrate, ethoxylated mono- and diglycerides, sorbitan monostearate, calcium stearyl-2-lactylate, sodium stearyl lactylate, lactylated fatty acid esters of glycerol and propylene glycerol, glycerol-lactoesters of $C_8$-$C_{24}$ fatty acids, polyglycerol esters of $C_8$-$C_{24}$ fatty acids, propylene glycol alginate, sucrose $C_8$-$C_{24}$ fatty acid esters, diacetyl tartaric and citric acid esters of mono- and diglycerides, triacetin, sarcosinate surfactants, isethionate surfactants, tautate surfactants, pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures thereof.

The surfactant, alone or in combination with other surfactants, may be present in oral compositions of the present invention in concentrations of about 0.001% to about 20% by weight of the total composition. In some embodiments, the surfactant may be present at about 0.05 to about 10% by weight of the total composition. Moreover, in some embodiments, the surfactant may be present in amounts of about 0.05 to about 2% by weight of the total composition.

Chelating Agents

As described above, the oral compositions of the present invention may include encapsulated chelating agents. Chelating agents strongly interact with metal ions, such as the calcium found in the cell walls of mouth bacteria. Chelating agents can also disrupt plaque by removing calcium from the calcium bridges which help hold this biomass intact.

One group of agents suitable for use as chelating agents in the compositions of the present invention are phosphate salts. In some embodiments, the phosphate salt selected from the following: pyrophosphates, triphosphates, polyphosphates, polyphosphonates and combinations thereof. The chelating agent can be a dialkali metal pyrophosphate salt, a tetra alkali polyphosphate salt or a combination thereof. For example, in some embodiments, the chelating agent can be selected from the following: tetrasodium pyrophosphate, tetrapotassium pyrophosphate, sodium tripolyphosphate, sodium hexametaphosphate and combinations of these. Other chelating agents that can be employed in the compositions of the present invention may include tartaric acid and salts thereof, citric acid and alkali metal citrates and mixtures thereof.

In some embodiments, the chelating agent is present in amounts of about 0.001 to about 5% by weight of the inventive oral composition. Furthermore, in some embodiments, the chelating agent is present in amounts of about 0.5 to about 3% by weight of the oral composition.

Hydrolytic Agents

In some embodiments the oral compositions of the present invention include encapsulated hydrolytic agents. Suitable hydrolytic agents include enzymes. For example, a protease, lipase, amylase for glucoamylase may be included in the invention compositions.

In some embodiments, the enzyme is present in amounts of about 0.01% to about 5.0% of the inventive oral composition. Furthermore, in some embodiments, the enzyme is present in amounts of about 0.01% to about 3.0%, or more specifically from about 0.1% to about 1.0% by weight of the oral composition.

Oxidizing Agents

The oral compositions of the present invention may include encapsulated oxidizing agents. Suitable oxidizing agents include peroxide compounds. Useful peroxides should contain an O-O bond, which can break down to provide at least one active specie. Examples of preferred peroxide compounds are inorganic peroxides, such as hydrogen peroxide, strontium peroxide, zinc peroxide or magnesium peroxide, and organic peroxides including, but not limited to, carbamide peroxide. The amount of the peroxide compound incorporated into the present composition will vary depending upon the particular individual or combinations of stain removing agents employed and the type of other components or components of the compositions and their respective amounts. The peroxide compound may be present in a stain removing effective amount of from about 0.01% to 10%, preferably from about 0.1% to 5%, and more preferably from about 0.2% to 3% by weight based on the total weight of the composition.

High Intensity Sweeteners

In some embodiments the oral compositions of the present invention include encapsulated high intensity sweeteners. High intensity sweeteners include sucralose, aspartame, neotame, salts of acesulfame, and the like. Such sweeteners are desirably present in amounts up to about 1.0% by weight of the oral composition.

Abrasive Agent

In some embodiments, the oral compositions of the present invention include an abrasive agent. Suitable abrasives include silicas, aluminas, phosphates, carbonates and combinations thereof. In some embodiments, the abrasive agent is a silica selected from: precipitated silica, silica gels and combinations thereof. Moreover, in some embodiments the abrasive agent is selected from the following: calcium carbonate, sodium bicarbonate, sodium metaphosphate, potassium metaphosphate, tricalcium phosphate, dehydrated dicalcium phosphate and combinations thereof.

The abrasive polishing material contemplated for use in the compositions of the present invention can be any material which does not excessively abrade dentin. However, silica dental abrasives have unique benefits of exceptional dental cleaning and polishing performance without unduly abrading tooth enamel or dentin.

The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in U.S. Pat. No. 3,538,230 to Pader, et al. and U.S. Pat. No. 3,862,307 to DiGiulio, both incorporated herein by reference in their entirety. Preferred are the silica xerogels marketed under the trade name "Syloid" by the W.R. Grace & Company, Davison Chemical Division. Also preferred are the precipitated silica materials, such as those marketed by the J.M. Huber Corporation under the trade name "Zeodent", particularly the silica carrying the designation "Zeodent 119". The types of silica dental abrasives useful in the present invention are described in detail in U.S. Pat. No. 4,340,583 to Wason, incorporated herein by reference in its entirety. Silica abrasives described in U.S. patent application Ser. Nos. 08/434,147 and 08/434,149, both filed May 2, 1995, are also herein incorporated by reference.

In some embodiments, an abrasive is present in amounts from about 0.1 to about 30% by weight of the oral composition. The abrasive agent may be more typically employed in amounts from about 0.5 to about 5% by weight of the total composition. The abrasive in the toothpaste compositions of this invention is generally present at a level of from about 0.5% to about 10% by weight of the composition. Moreover, inventive chewing gum may contain from about 1% to about 6% of abrasive, by weight of the oral composition.

The silica used to prepare a chewing gum composition of the present invention is differentiated by means of its oil absorption value, having oil absorption value of less than 100 cc/100 g, and preferably in the range of from 45 cc/100 g silica to less than 70 cc/100 g silica. Silica particularly useful in the practice of the present invention is marketed under the trade designation SYLODENT XWA GRACE Davison Co., Columbia, DS 21044. An example of such silica is SYLODENT XWA 150, a silica precipitate having a water content of 4.7% by weight averaging from about 7 to about 11 microns in diameter, having an Einlehner Hardness of 5, a BET surface area of 390 m$^2$/g of silica, an oil absorption of less than 70 cm$^3$/100 g of silica. This silica exhibits low abrasiveness to tooth enamel.

A silica abrasive can be used as the sole abrasive in preparing a chewing gum of the present invention or in combination with other known abrasives or polishing agents, including calcium carbonate, sodium bicarbonate, sodium metaphosphate, potassium metaphosphate, tricalcium phosphate, dehydrated dicalcium phosphate, or other siliceous materials, or combinations thereof.

In some embodiments, the total quantity of abrasive silica present in a chewing gum composition of the present invention is at a concentration of from about 0.1 to about 20% by weight. Moreover, in some embodiments, the total quantity of abrasive silica present in a chewing gum composition of the present invention is from about 0.5% to about 5% by weight.

Orally Acceptable Carrier Composition

The oral compositions of the present invention include an orally acceptable carrier composition, in an appropriate amount to accommodate the other components of the formulation. The term "orally acceptable carrier composition" refers to a vehicle capable of being mixed with the active components for delivery to the oral cavity for tooth whitening and cleaning purposes, and which will not cause harm to warm-blooded animals, including humans. The orally acceptable carriers further include those components of the composition that are capable of being comingled without interaction in a manner which would substantially reduce the composition's stability and/or efficacy for dental stain-removal in the oral cavity of warm-blooded animals, including humans, in accordance with the compositions and methods of the present invention.

The orally acceptable carriers of the present invention can include one or more compatible solid or liquid filler diluents or encapsulating substances, which are suitable for oral administration. The carriers or excipients employed in the present invention may be in any form appropriate to the mode of delivery, for example, solutions, colloidal dispersions, emulsions, suspensions, rinses, gels, foams, powders, solids, and the like, and can include conventional components of toothpastes (including gels), mouthwashes and rinses, mouth sprays, chewing gums, lozenges, and confectionaries. Carriers suitable for the preparation of compositions of the present invention are well known in the art. Their selection will depend on secondary considerations like taste, cost, shelf stability and the like.

Types of additives or ingredients, which may be included in the present compositions include one or more desirable stain-removing agents as provided herein. The inventive compositions may also include a component selected from the following: elastomers, elastomer solvents, waxes, emulsifiers, plasticizers, softeners, dispersing agents, sweeteners, flavorants, humectants, active agents, cooling agents, warming agents, tooth whitening agents, colorants, bulking agents, fillers and combinations thereof.

In some embodiments, an active agent can be a fluoride compound or an antibacterial compound. For example, a known antibacterial compound is triclosan.

Moreover, in some embodiments a film-forming polymer may be included in the compositions of the present invention. For example, the film-forming polymer may be a synthetic anionic polymeric polycarboxylate (SAPP), such a PVM/MA copolymer (Gantrez S-97, GAF Corp.). Such polymers are described in U.S. Pat. Nos. 5,334,375 and 5,505,933, which are incorporated by reference herein in their entirety. SAPP's have previously been described as being useful for dentin sensitivity reduction. Moreover, SAPP's have previously been described as antibacterial-enhancing agents, which enhance delivery of an antibacterial agent to oral surfaces, and which enhance the retention of the antibacterial agent on oral surfaces. It is well within the contemplation of the present invention that film-forming polymers, such as PVM/MA copolymer, may be employed in the compositions of the present invention as a means of reducing stain formation.

As described above, in some embodiments, the inventive composition may be a gum composition including a gum base and the encapsulated active.

As described above, in some embodiments, the inventive composition may be a gum composition including a gum base and the encapsulated active. The gum base may be present in an amount of about 20 to about 40% by weight of the total composition. It may include any component known in the chewing gum art. For example, the gum base may include sweeteners, elastomers, bulking agents, waxes, elastomer solvents, emulsifiers, plasticizers, fillers, mixtures thereof and may include a desirable stain-removing agent(s) as provided herein.

In some embodiments, the gum base may include a suitable sugar bulking agent. For example, the gum base may include a specific polyol composition including at least one polyol which is from about 30% to about 80% by weight of the gum base, and desirably from 50% to about 60%. The polyol composition may include any polyol known in the art including, but not limited to maltitol, sorbitol, erythritol, xylitol, mannitol, isomalt, lactitol and combinations thereof. Lycasin which is a hydrogenated starch hydrolysate including sorbitol and maltitol, may also be used.

The elastomers (rubbers) employed in the gum base will vary greatly depending upon various factors such as the type of gum base desired, the consistency of gum composition desired and the other components used in the composition to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base compositions include, without limitation, natural substances (of vegetable origin) such as chicle, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

The amount of elastomer employed in the gum base may vary depending upon various factors such as the type of gum base used, the consistency of the gum composition desired and the other components used in the composition to make the final chewing gum product. In general, the elastomer will be present in the gum base in an amount from about 10% to about 60% by weight of the gum region, desirably from about 35% to about 40% by weight.

When a wax is present in the gum base, it softens the polymeric elastomer mixture and improves the elasticity of the gum base. The waxes employed will have a melting point below about 60° C., and preferably between about 45° C. and about 55° C. The low melting wax may be a paraffin wax. The wax may be present in the gum base in an amount from about 6% to about 10%, and preferably from about 7% to about 9.5%, by weight of the gum base.

In addition to the low melting point waxes, waxes having a higher melting point may be used in the gum base in amounts up to about 5%, by weight of the gum base. Such high melting waxes include beeswax, vegetable wax, candelilla wax, carnuba wax, most petroleum waxes, and the like, and mixtures thereof.

In addition to the components set out above, the gum base may include a variety of other components, such as components selected from elastomer solvents, emulsifiers, plasticizers, fillers, and mixtures thereof.

The gum base may contain elastomer solvents to aid in softening the elastomer component. Such elastomer solvents may include those elastomer solvents known in the art, for example, terpinene resins such as polymers of alpha-pinene or beta-pinene, methyl, glycerol and pentaerythritol esters of rosins and modified rosins and gums such as hydrogenated, dimerized and polymerized rosins, and mixtures thereof. Examples of elastomer solvents suitable for use herein may include the pentaerythritol ester of partially hydrogenated wood and gum rosin, the pentaerythritol ester of wood and gum rosin, the glycerol ester of wood rosin, the glycerol ester of partially dimerized wood and gum rosin, the glycerol ester of polymerized wood and gum rosin, the glycerol ester of tall oil rosin, the glycerol ester of wood and gum rosin and the partially hydrogenated wood and gum rosin and the partially hydrogenated methyl ester of wood and rosin, and the like, and mixtures thereof. The elastomer solvent may be employed in the gum base in amounts from about 2% to about 15%, and preferably from about 7% to about 11%, by weight of the gum base.

The gum base may also include emulsifiers which aid in dispersing any immiscible components into a single stable system. The emulsifiers useful in this invention include glyceryl monostearate, lecithin, fatty acid monoglycerides, diglycerides, propylene glycol monostearate, and the like, and mixtures thereof. The emulsifier may be employed in amounts from about 2% to about 15%, and more specifically, from about 7% to about 11%, by weight of the gum base.

The gum base may also include plasticizers or softeners to provide a variety of desirable textures and consistency properties. Because of the low molecular weight of these components, the plasticizers and softeners are able to penetrate the fundamental structure of the gum base making it plastic and less viscous. Useful plasticizers and softeners include lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, and the like, and mixtures thereof. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like, may also be incorporated into the gum base. The plasticizers and softeners are generally employed in the gum base in amounts up to about 20% by weight of the gum base, and more specifically in amounts from about 9% to about 17%, by weight of the gum base.

Plasticizers also include are the hydrogenated vegetable oils and include soybean oil and cottonseed oil which may be employed alone or in combination. These plasticizers provide the gum base with good texture and soft chew characteristics. These plasticizers and softeners are generally employed in amounts from about 5% to about 14%, and more specifically in amounts from about 5% to about 13.5%, by weight of the gum base.

Anhydrous glycerin may also be employed as a softening agent, such as the commercially available United States Pharmiacopeia (USP) grade. Glycerin is a syrupy liquid with a sweet warm taste and has a sweetness of about 60% of that of cane sugar. Because glycerin is hygroscopic, the anhydrous glycerin may be maintained under anhydrous conditions throughout the preparation of the chewing gum composition.

Although softeners may be present to modify the texture of the gum composition, they may be present in reduced amounts as compared to typical gum compositions. For example, they may be present from about 0.5 to about 10% by weight based on the total weight of the composition, or they may not be present in the composition, since a surfactant active can act as a softener.

The gum base of this invention may also include effective amounts of bulking agents such as mineral adjuvants, which may serve as fillers and textural agents. Useful mineral adjuvants include calcium carbonate, magnesium carbonate, alumina, aluminum hydroxide, aluminum silicate, talc, tricalcium phosphate, dicalcium phosphate, calcium sulfate and the like, and mixtures thereof. These fillers or adjuvants may be used in the gum base compositions in various amounts. Preferably the amount of filler, when used, will be present in an amount from about 15% to about 40%, and desirably from about 20% to about 30%, by weight of the gum base.

A variety of traditional additives may be optionally included in the gum base in effective amounts such as coloring agents, antioxidants, preservatives, flavoring agents, and the like. For example, titanium dioxide and other dyes suitable for food, drug and cosmetic applications, known as F. D. & C. dyes, may be utilized. An anti-oxidant such as butylated hydroxytoluene (BHT), butylated hydroxyanisole (BHA), propyl gallate, and mixtures thereof, may also be included. Other conventional chewing gum additives known to one having ordinary skill in the chewing gum art may also be used in the gum base.

Some embodiments extend to methods of making the gum compositions. The manner in which the gum base components are mixed is not critical and is performed using standard techniques and apparatus known to those skilled in the art. In a typical method, an elastomer is admixed with an elastomer solvent and/or a plasticizer and/or an emulsifier and agitated for a period of from 1 to 30 minutes. The remaining components, such as the low melting point wax, are then admixed, either in bulk or incrementally, while the gum base mixture is blended again for 1 to 30 minutes.

The gum composition may include amounts of conventional additives selected from, but not limited to, the following: sweetening agents (sweeteners), plasticizers, softeners, emulsifiers, waxes, fillers, bulking agents (carriers, extenders, bulk sweeteners), mineral adjuvants, flavoring agents (flavors, flavorings), coloring agents (colorants, colorings), antioxidants, acidulants, thickeners, medicaments, and the like, and mixtures thereof. Some of these additives may serve more than one purpose. For example, in sugarless gum compositions, a sweetener, such as maltitol or other sugar alcohol, may also function as a bulking agent.

The plasticizers, softening agents, mineral adjuvants, waxes and antioxidants discussed above, as being suitable for use in the gum base, may also be used in the chewing gum composition. Examples of other conventional additives which may be used include emulsifiers, such as lecithin and glyceryl monostearate, thickeners, used alone or in combination with other softeners, such as methyl cellulose, alginates, carrageenan, xanthan gum, gelatin, carob, tragacanth, locust bean, and carboxy methyl cellulose, acidulants such as malic acid, adipic acid, citric acid, tartaric acid, fumaric acid, and mixtures thereof, and fillers, such as those discussed above under the category of mineral adjuvants.

In some embodiments, the gum region may also contain a bulking agent. Suitable bulking agents may be water-soluble and include sweetening agents selected from, but not limited to, monosaccharides, disaccharides, polysaccharides, sugar alcohols, and mixtures thereof; randomly bonded glucose polymers such as those polymers distributed under the tradename POLYDEXTROSE by Pfizer, Inc., Groton, Conn.; isomalt (a racemic mixture of alpha-D-glucopyranosyl-1,6-mannitol and alpha-D-glucopyranosyl-1,6-sorbitol manufactured under the tradename PALATINIT by Suddeutsche Zucker), maltodextrins; hydrogenated starch hydrolysates; hydrogenated hexoses; hydrogenated disaccharides; minerals, such as calcium carbonate, talc, titanium dioxide, dicalcium phosphate; celluloses; and mixtures thereof.

Suitable sugar bulking agents include monosaccharides, disaccharides and polysaccharides such as xylose, ribulose, glucose (dextrose), mannose, galactose, fructose (levulose), sucrose (sugar), maltose, invert sugar, partially hydrolyzed starch and corn syrup solids, and mixtures thereof.

Suitable sugar alcohol bulking agents include sorbitol, xylitol, mannitol, galactitol, maltitol, and mixtures thereof.

Suitable hydrogenated starch hydrolysates include those disclosed in U.S. Pat. Nos. 25,959, 3,356,811, 4,279,931 and various hydrogenated glucose syrups and/or powders which contain sorbitol, hydrogenated disaccharides, hydrogenated higher polysaccharides, or mixtures thereof. Hydrogenated starch hydrolysates are primarily prepared by the controlled catalytic hydrogenation of corn syrups. The resulting hydrogenated starch hydrolysates are mixtures of monomeric, dimeric, and polymeric saccharides. The ratios of these different saccharides give different hydrogenated starch hydrolysates different properties. Mixtures of hydrogenated starch hydrolysates, such as LYCASIN, a commercially available product manufactured by Roquette Freres of France, and HYSTAR, a commercially available product manufactured by Lonza, Inc., of Fairlawn, N.J., are also useful.

The sweetening agents used may be selected from a wide range of materials including water-soluble sweeteners, water-soluble artificial sweeteners, water-soluble sweeteners derived from naturally occurring water-soluble sweeteners, dipeptide based sweeteners, and protein based sweeteners, including mixtures thereof. Without being limited to particular sweeteners, representative categories and examples include:

(a) water-soluble sweetening agents such as dihydrochalcones, monellin, steviosides, glycyrrhizin, dihydroflavenol, and sugar alcohols such as sorbitol, mannitol, maltitol, and L-aminodicarboxylic acid aminoalkenoic acid ester amides, such as those disclosed in U.S. Pat. No. 4,619,834, which disclosure is incorporated herein by reference, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and mixtures thereof;

(c) dipeptide based sweeteners, such as L-aspartic acid derived sweeteners, such as L-aspartyl-L-phenylalanine methyl ester (Aspartame), N—[N-(3,3-dimethylbutyl)-L-α-aspartyl]-L-phenylalanine 1-methyl ester (Neotame), and materials described in U.S. Pat. No. 3,492,131, L-alphaaspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and mixtures thereof;

(d) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalactosucrose derivatives include but are not limited to: 1-chloro-1'-deoxysucrose; 4-chloro-4-deoxy-alpha-D-galactopyranosyl-alpha-D-fructofuranoside, or 4-chloro-4-deoxygalactosucrose; 4-chloro-4-deoxy-alpha-D-galactopyranosyl-1-chloro-1-deoxy-beta-D-fructofuranoside, or 4,1'-dichloro-4,1'-dideoxygalactosucrose;

1',6'-dichloro1',6'-dideoxysucrose; 4-chloro-4-deoxy-alpha-D-galactopyranosyl-1,6-dichloro-1,6-dideoxy-beta-D-fructofuranoside, or 4,1',6'-trichloro-4,1',6'-trideoxygalactosucrose; 4,6-dichloro-4,6-dideoxy-alpha-D-galactopyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galactopyranosyl-1,6-dichloro-1,6-dideoxy-beta-D-fructofuranoside, or 4,6,1',6'-tetrachloro4,6,1',6'-tetradeoxygalacto-sucrose; and 4,6,1',6'-tetradeoxy-sucrose, and mixtures thereof; and (e) protein based sweeteners such as thaumaoccous danielli (Thaumatin I and II).

The intense sweetening agents may be used in many distinct physical forms well-known in the art to provide an initial burst of sweetness and/or a prolonged sensation of sweetness. Without being limited thereto, such physical forms include free forms, such as spray dried, powdered, beaded forms, encapsulated forms, and mixtures thereof.

Desirably, the sweetener is a high intensity sweetener such as aspartame, sucralose, and acesulfame potassium (Ace-K).

In general, an effective amount of sweetener may be utilized to provide the level of sweetness desired, and this amount may vary with the sweetener selected. The amount of sweetener may be present in amounts from about 0.001% to about 3%, by weight of the gum composition, depending upon the sweetener or combination of sweeteners used. The exact range of amounts for each type of sweetener may be selected by those skilled in the art.

The flavoring agents which may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Nonlimiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, spearmint, artificial vanilla, cinnamon derivatives, and various fruit flavors, whether employed individually or in admixture.

Other useful flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, publication 1274, pages 63-258, by the National Academy of Sciences, may be used. This publication is incorporated herein by reference.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, strawberry shortcake, and mixtures thereof.

In some embodiments, the flavoring agent may be employed in either liquid form and/or dried form. When employed in the latter form, suitable drying means such as spray drying the oil may be used. Alternatively, the flavoring agent may be absorbed onto water soluble materials, such as cellulose, starch, sugar, maltodextrin, gum arabic and so forth or may be encapsulated. The actual techniques for preparing such dried forms are well-known.

In some embodiments, the flavoring agents may be used in many distinct physical forms well-known in the art to provide an initial burst of flavor and/or a prolonged sensation of flavor. Without being limited thereto, such physical forms include free forms, such as spray dried, powdered, beaded forms, encapsulated forms, and mixtures thereof.

The amount of flavoring agent employed herein may be a matter of preference subject to such factors as the type of final chewing gum composition, the individual flavor, the gum base employed, and the strength of flavor desired. Thus, the amount of flavoring may be varied in order to obtain the result desired in the final product and such variations are within the capabilities of those skilled in the art without the need for undue experimentation. In gum compositions, the flavoring agent is generally present in amounts from about 0.02% to about 5%, and more specifically from about 0.1% to about 2%, and even more specifically, from about 0.8% to about 1.8%, by weight of the chewing gum composition.

Coloring agents may be used in amounts effective to produce the desired color. The coloring agents may include pigments which may be incorporated in amounts up to about 6%, by weight of the gum composition. For example, titanium dioxide may be incorporated in amounts up to about 2%, and preferably less than about 1%, by weight of the gum composition. The colorants may also include natural food colors and dyes suitable for food, drug and cosmetic applications. These colorants are known as F.D.& C. dyes and lakes. The materials acceptable for the foregoing uses are preferably water-soluble. Illustrative nonlimiting examples include the indigoid dye known as F.D.& C. Blue No. 2, which is the disodium salt of 5,5-indigotindisulfonic acid. Similarly, the dye known as F.D.& C. Green No. 1 comprises a triphenylmethane dye and is the monosodium salt of 4-[4-(N-ethyl-p-sulfoniumbenzylamino)diphenylmethylene]-[1-(N-ethyl-N-p-sulfoniumbenzyl)-delta-2,5-cyclohexadieneimine]. A full recitation of all F.D.& C. colorants and their corresponding chemical structures may be found in the Kirk-Othmer Encyclopedia of Chemical Technology, 3rd Edition, in volume 5 at pages 857-884, which text is incorporated herein by reference.

Suitable oils and fats usable in gum compositions include partially hydrogenated vegetable or animal fats, such as coconut oil, palm kernel oil, beef tallow, and lard, among others. These components when used are generally present in amounts up to about 7%, and preferably up to about 3.5%, by weight of the gum composition.

Some embodiments may include a method for preparing the gum compositions, including both chewing gum and bubble gum compositions. The chewing gum compositions may be prepared using standard techniques and equipment known to those skilled in the art. The apparatus useful in accordance with some embodiments comprises mixing and heating apparatus well known in the chewing gum manufacturing arts, and therefore the selection of the specific apparatus will be apparent to the artisan.

In some embodiments, a method of preparing a tooth whitening gum composition includes encapsulating a tooth whitening active component of the composition within a reactive barrier coating. The coating includes a hydrophilic material; and a component reactive with a stability-limiting component in the gum composition. The method also includes heating a gum base to soften the base and then mixing the softened gum base with the encapsulated tooth whitening active component so as to obtain a substantially homogeneous mixture. The method further includes cooling the mixture and forming the cooled mixture into individual gum pieces. Further components may be mixed into the softened gum base. For example, one or more of the following may typically be added: bulking agent, filler, humectant, flavorant, colorant, dispersing agent, softener, plasticizer, preservative, warming agent, cooling agent, tooth whitening agent and sweetener.

In some embodiments, the method of preparing a tooth whitening gum composition of the present invention can involve suspending tooth whitening active particles in a fluidized air stream; and spraying a reactive barrier coating onto the suspended active particles. The coating includes a hydrophilic material and a component reactive with a stability-limiting component in the gum. Suitable tooth whitening actives are the same as those described above. Moreover, suitable hydrophilic materials and reactive components for the barrier coating are the same as those described above. One or more barrier coating layers may be sprayed onto the suspended active particles. The coating composition sprayed on the particles may include any solvent capable of dissolving the water-soluble hydrophilic material in the coating.

The encapsulated particles of some embodiments may be prepared by any suitable spray coating method as known in the art. One suitable process is the Wurster process. This process provides a method for encapsulating individual particulate materials. First the particles to be encapsulated are suspended in a fluidizing air stream which provides a generally cyclic flow in front of a spray nozzle. The spray nozzle sprays an atomized flow of the coating solution.

The atomized barrier coating solution collides with the particles as they are carried away from the nozzle to provide a particle coating with the coating solution. The temperature of the fluidizing air stream, which also serves to suspend the particles to be coated, may be adjusted to evaporate the solvent shortly after the coating solution contacts the particles. This serves to solidify the coating on the particles, resulting in the desired encapsulated particle.

This process may be repeated until the desired thickness of the barrier coating is achieved. Alternatively, the process may be repeated with a different barrier coating solution to provide different and distinct barrier coating layers in the encapsulated particle composition.

Following the barrier coating process, the particles may then be formed to an appropriate size as desired, generally from an average particle size range of about 50 μm to about 800 μm. This may be accomplished by any suitable means such as chopping, pulverizing, milling or grinding the particles.

In some embodiments, gum pieces may be coated with an aqueous gum coating composition, which may be applied by any method known in the art. The gum coating composition may be present in an amount from about 25% to about 35% by weight of the total gum piece, more specifically about 30% by weight of the gum piece.

The outer gum coating may be hard or crunchy. Typically, the outer gum coating may include sorbitol, maltitol, xylitol, isomalt, and other crystallizable polyols; sucrose may also be used. Flavors may also be added to yield unique product characteristics. Moreover, the outer gum coating may include one or more of the encapsulated active agents provided herein.

The gum coating, if present, may include several opaque layers, such that the chewing gum composition is not visible through the coating itself, which can optionally be covered with a further one or more transparent layers for aesthetic, textural and protective purposes. The outer gum coating may also contain small amounts of water and gum arabic. The gum coating can be further coated with wax. The gum coating may be applied in a conventional manner by successive applications of a coating solution, with drying in between each coat. As the coating dries it usually becomes opaque and is usually white, though other colorants may be added. A polyol coating can be further coated with wax. The gum coating can further include colored flakes or speckles.

If the composition comprises a gum coating, it is possible that one or more oral care actives can be dispersed throughout the coating. This may be preferred if one or more oral care actives is incompatible in a single phase composition with another of the actives. Moreover, it is well within the contemplation of the present invention that providing one or more of the stain-removing agents in the gum coating can enhance the stain-removing efficacy of the total composition.

The encapsulated active can be included in one or more of the chewing gum regions such as the gum coating, the gum base or both. Additionally, the encapsulated active can be added at different stages of the manufacture, alone or as a premix with other components. For example, in some embodiments, the method for preparing a stain-removing gum composition includes heating a gum base to soften the base; and mixing the softened gum base with at least one of the following: elastomer, wax, emulsifier, bulking agent, filler, humectant, flavorant, colorant, dispersing agent, softener, plasticizer, preservative, warming agent, cooling agent, tooth whitening agent and sweetener to obtain a substantially homogeneous mixture. The method also involves cooling the mixture; forming the cooled mixture into individual gum pieces; and coating the gum pieces with a gum coating solution including the encapsulated active. The hydroxy fatty acid salt may be a salt of ricinoleic acid. One or more other components may be included in the gum coating, such as including, but not limited to, the following: gum arabic, flavorant, colorant, sweetener, bulking agent, filler, anti-adherent compound, dispersing agent, moisture absorbing compound, warming agent, cooling agent and film-forming agent.

The gum coating may be formulated to assist with increasing the thermal stability of the gum piece and preventing leaking of a liquid fill if the gum product is a center-filled gum. In some embodiments, the gum coating may include a gelatin composition. The gelatin composition may be added as a 40% by weight solution and may be present in the gum coating composition from about 5% to about 10% by weight of the gum coating composition, and more specifically about 7% to about 8%. The gel strength of the gelatin may be from about 130 bloom to about 250 bloom.

Additives, such as physiological cooling agents, throat-soothing agents, spices, warming agents, tooth-whitening agents, breath-freshening agents, vitamins minerals, caffeine, drugs and other actives may be included in any or all portions of the chewing gum composition. Such components may be used in amounts sufficient to achieve their intended effects.

With respect to cooling agents, a variety of well known cooling agents may be employed. For example, among the useful cooling agents are included menthol, xylitol, menthane, menthone, menthyl acetate, menthyl salicylate, N,2,3-trimethyl-2-isopropyl butanamide (WS-23), N-ethyl-p-menthane-3-carboxamide (WS-3), menthyl succinate, 3,1-menthoxypropane 1,2-diol, among others. These and other suitable cooling agents are further described in the following U.S. patents, all of which are incorporated in their entirety by reference hereto: U.S. Pat. Nos. 4,230,688 and 4,032,661 to Rowsell et al.; 4,459,425 to Amano et al.; 4,136,163 to Watson et al.; and 5,266,592 to Grub et al. These cooling agents may be present in one or more of the outer gum coatings, the gum region surrounding the liquid fill, the liquid fill per se, or in any combination of those three gum areas. Cooling agents, when used in the outer coating composition for the gum, are generally present in amount of 0.01% to about 1.0%. When used in the other portions of the gum, such as the gum region or the center fill, they may be present in amounts of about 0.001 to about 10% by weight of the total chewing gum piece.

Warming components may be selected from a wide variety of compounds known to provide the sensory signal of warming to the user. These compounds offer the perceived sensation of warmth, particularly in the oral cavity, and often enhance the perception of flavors, sweeteners and other organoleptic components. Among the useful warming compounds included are vanillyl alcohol n-butylether (TK-1000) supplied by Takasago Perfumary Company Limited, Tokyo, Japan, vanillyl alcohol n-propylether, vanillyl alcohol isopropylether, vanillyl alcohol isobutylether, vanillyl alcohol n-aminoether, vanillyl alcohol isoamyleather, vanillyl alcohol n-hexyleather, vanillyl alcohol methylether, vanillyl alcohol ethyleather, gingerol, shogaol, paradol, zingerone, capsaicin, dihydrocapsaicin, nordihydrocapsaicin, homocapsaicin, homodihydrocapsaicin, ethanol, isopropol alcohol, iso-amylalcohol, benzyl alcohol, glycerine, and combinations thereof.

The features and advantages of the present invention are more fully shown by the following examples which are provided for purposes of illustration, and are not to be construed as limiting the invention in any way.

EXAMPLES

Example 1 Encapsulation of Polyphosphates

Polyphosphate=Sodium tripolyphosphate (STP)
Step 1: Reactive barrier coating system pH=7.4

| | |
|---|---|
| Water | 78.807% |
| Gum Arabic | 20% |
| Monosodium phosphate, monohydrate | 0.1558% |
| Disodium phosphate, heptahydrate | 1.0374% |

Dissolve gum Arabic and phosphate salts in water while stirring. The pH of the resulting solution should be 7.4. Spray coat STP using the above solution to 10% by weight using standard Fludized Bed equipment.
Step 2: Physical barrier coating system

| | |
|---|---|
| Water | 80% |
| Gum Arabic | 20% |

Dissolve gum Arabic in water while stirring. Spray coat STP to additional of 20% coating.
Total coating=10+20=30% by weight Chewing Gum Preparation Containing Encapsulated STP A chewing gum composition was prepared using encapsulated STP prepared in example 1. The chewing gum components are shown in Table 2.

TABLE 2

| Chewing gum | |
|---|---|
| Components | % |
| Gum base | 39.0 |
| Sorbitol | QS |
| Mannitol | 9.0 |
| Flavor | 4.67 |
| Glycerin | 1.5 |
| Lecithin | 0.2 |
| Encapsulated STP | 2.83 |
| Total | 100 |

The chewing gum composition was prepared as follows. The gum base was melted at a suitable temperature in a mixer. The remaining components were then added to the melted gum base and mixed until the components were completely dispersed. The resulting chewing gum composition was sized.

Example 2 Encapsulation of Phosphate Salts

Enzyme=Papain
Step 1: Reactive barrier coating system pH=6.5

| | |
|---|---|
| Water | 79.114% |
| Gum Arabic | 20% |
| Monosodium phosphate, monohydrate | 0.482% |
| Disodium phosphate, heptahydrate | 0.4039% |

Dissolve gum Arabic and phosphate salts in water while stirring. The pH of the resulting solution should be 6.5. Spray coat papain using the above solution to 10% by weight using standard Fludized Bed equipment.
Step 2: Physical barrier coating system

| | |
|---|---|
| Water | 80% |
| Gum Arabic | 20% |

Dissolve gum Arabic in water while stirring. Spray coat papain to additional of 20% coating.
Total coating=10+20=30% by weight Chewing Gum Preparation Containing Encapsulated Papain A chewing gum composition was prepared using encapsulated papain prepared in example 2. The chewing gum components are shown in Table 3.

TABLE 3

| Chewing gum compositions | |
|---|---|
| Component | % |
| Gum base | 39.0 |
| Sorbitol | QS |
| Mannitol | 9.0 |
| Flavor | 4.67 |
| Glycerin | 1.5 |
| Lecithin | 0.2 |
| Encapsulated Papain | 0.12 |
| Total | 100 |

The chewing gum composition was prepared as follows. The gum base was melted at a suitable temperature in a mixer. The remaining components were then added to the melted gum base and mixed until the components were completely dispersed. The resulting chewing gum composition was sized.

Example 3 Encapsulation of Surfactants

Surfactant=Sodium Stearate
Step 1: Reactive barrier coating system pH=8.0

| Water | 78.114% |
|---|---|
| Gum Arabic | 20% |
| Monosodium phosphate, monohydrate | 0.4712% |
| Disodium phosphate, heptahydrate | 1.2485% |

Dissolve gum Arabic and phosphate salts in water while stirring. The pH of the resulting solution should be 8.0. Spray coat Sodium Stearate using the above solution to 10% by weight using standard Fludized Bed equipment.
Step 2: Physical barrier coating system

| Water | 80% |
|---|---|
| Gum Arabic | 20% |

Dissolve gum Arabic in water while stirring. Spray coat Sodium Stearate to additional of 20% coating.
Total coating=10+20=30% by weight
Chewing Gum Preparation Containing Encapsulated Sodium stearate A chewing gum composition was prepared using encapsulated sodium stearate prepared in example 3. The chewing gum components are shown in Table 4.

TABLE 4

| Chewing gum compositions | |
|---|---|
| Component | Chewing Gum 1 |
| Gum base | 39.0 |
| Sorbitol | QS |
| Mannitol | 9.0 |
| Flavor | 4.67 |
| Glycerin | 1.5 |
| Lecithin | 0.2 |
| Encapsulated Sodium Stearate | 1.4 |
| Total | 100 |

The chewing gum composition was prepared as follows. The gum base was melted at a suitable temperature in a mixer. The remaining components were then added to the melted gum base and mixed until the components were completely dispersed. The resulting chewing gum composition was sized.

Example 4 Encapsulation of Peroxides

Peroxide=Carbamide Peroxide
Step 1: Reactive barrier coating system pH=6.0

| Water | 79.23% |
|---|---|
| Gum Arabic | 20% |
| Monosodium phosphate, monohydrate | 0.607% |
| Disodium phosphate, heptahydrate | 0.161% |

Dissolve gum Arabic and phosphate salts in water while stirring. The pH of the resulting solution should be 6.0. Spray coat carbamide peroxide using the above solution to 10% by weight using standard Fludized Bed equipment.
Step 2: Physical barrier coating system

| Water | 80% |
|---|---|
| Gum Arabic | 20% |

Dissolve gum Arabic in water while stirring. Spray coat carbamide peroxide to additional of 20% coating.
Total coating=10+20=30% by weight
Chewing Gum Preparation Containing Encapsulated Carbamide Peroxide A chewing gum composition was prepared using encapsulated carbamide peroxide prepared in example 4. The chewing gum components are shown in Table 5.

TABLE 5

| Chewing gum compositions | |
|---|---|
| Component | % |
| Gum base | 39.0 |
| Sorbitol | QS |
| Mannitol | 9.0 |
| Flavor | 4.67 |
| Glycerin | 1.5 |
| Lecithin | 0.2 |
| Encapsulated Carbamide Peroxide | 3.0 |
| Total | 100 |

The chewing gum composition was prepared as follows. The gum base was melted at a suitable temperature in a mixer. The remaining components were then added to the melted gum base and mixed until the components were completely dispersed. The resulting chewing gum composition was sized.

Example 5 Encapsulation of Sweeteners

Sweetener=Neotame
Step 1: Reactive barrier coating system pH=4.0

| Water | 79.50% |
|---|---|
| Gum Arabic | 20% |
| Citric acid, anhydrous | 0.17% |
| Sodium citrate, dihydrate | 0.15% |

Dissolve gum Arabic and citric acid and citrate salt in water while stirring. The pH of the resulting solution should be 4.0. Spray coat neotame using the above solution to 10% by weight using standard Fludized Bed equipment.
Step 2: Physical barrier coating system

| Water | 80% |
|---|---|
| Gum Arabic | 20% |

Dissolve gum Arabic in water while stirring. Spray coat Neotame to additional of 20% coating.
Total coating=10+20=30% by weight
Chewing Gum Preparation Containing Encapsulated Neotame A chewing gum composition was prepared using encapsulated neotame prepared in example 5. The chewing gum components are shown in Table 6.

TABLE 6

Chewing gum compositions

| Component | % |
|---|---|
| Gum base | 39.0 |
| Sorbitol | QS |
| Mannitol | 9.0 |
| Flavor | 4.67 |
| Glycerin | 1.5 |
| Lecithin | 0.2 |
| Encapsulated Neotame | 0.06 |
| Total | 100 |

The chewing gum composition was prepared as follows. The gum base was melted at a suitable temperature in a mixer. The remaining components were then added to the melted gum base and mixed until the components were completely dispersed. The resulting chewing gum composition was sized.

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. An oral composition having an increased shelf life comprising:
   (a) a carrier composition comprising at least one first reactive component, wherein the carrier composition is selected from the group consisting of a gum base, a confectionary base, a toothpaste base, a gel dentifrice base and a tooth powder base; and
   (b) an active composition comprising at least one active component encapsulated in a coating, wherein said at least one active component comprises a peroxide, said coating comprising:
      (i) a physical barrier coating comprising gum arabic; and
      (ii) a reactive barrier coating comprising gum arabic and one or more phosphate salt,
      wherein the first reactive component is selected from the group consisting of acids, flavors, lecithin, peroxides, fluorides, water, aldehydes and glycerin; and
      wherein said coating provides an interaction of the first reactive component and the one or more phosphate salt, wherein said interaction prevents a degradation of the peroxide by controlling the pH of the first reactive component and provides an increased shelf life of the oral composition of at least one year as measured by the presence of at least 75% of the peroxide remaining, or,
      the interaction of the first reactive component and the one or more phosphate salt provides an increased shelf-life of the oral composition of at least six months as measured by the presence of at least 90% of the peroxide remaining.

2. The oral composition of claim 1, wherein the increased shelf-life of the oral composition is maintained for at least one year as measured by the presence of at least 75% of the active remaining.

3. The oral composition of claim 1, wherein the increased shelf-life of the oral composition is maintained for at least six months as measured by the presence of at least 90% of the active remaining.

4. The oral composition of claim 1, wherein the first reactive component is an acid.

5. The oral composition of claim 1, wherein the first reactive component is selected from the group consisting of flavorants, aldehydes and glycerin.

6. The oral composition of claim 1, wherein the composition is a gum composition.

7. The oral composition of claim 1, wherein the composition is a lozenge composition.

8. The oral composition of claim 1, wherein the composition is a mint composition.

9. The oral composition of claim 1, wherein the composition is a candy composition.

10. The oral composition of claim 1, wherein the composition is a toothpaste composition.

11. The oral composition of claim 1, wherein the composition is a gel dentifrice composition.

12. The oral composition of claim 1, wherein the composition is mouthrinse or mouthwash composition.

13. The oral composition of claim 1, wherein the composition is a tooth powder composition.

14. A tooth whitening gum composition having an increased shelf life comprising:
   (a) a gum base, said gum base comprising at least one first reactive component, which upon exposure to one or more active components, reacts therewith to reduce the activity of one or more active components; and
   (b) an active composition comprising at least one active component, wherein said at least one active component comprises a peroxide, encapsulated in a coating, said coating comprising:
      (i) a physical barrier coating comprising gum arabic; and
      (ii) a reactive barrier coating comprising gum arabic and one or more phosphate salt,
      wherein the first reactive component is selected from the group consisting of acids, flavors, lecithin, peroxides, fluorides, water, aldehydes and glycerin; and
      wherein said coating provides an interaction of the first reactive component and the one or more phosphate salt,
      wherein said interaction provides an increased shelf life of the tooth whitening gum composition of at least one year as measured by the presence of at least 75% of the peroxide remaining, or,
      provide a shelf-life of the tooth whitening gum composition of at least six months as measured by the presence of at least 90% of the peroxide remaining.

15. A tooth whitening gum composition having an increased shelf life comprising:
   (a) a gum base, said gum base comprising at least one first reactive component, which upon exposure to one or more active components, reacts therewith to reduce the activity of one or more active components; and
   (b) an active composition comprising at least one active component wherein said at least one active component comprises a peroxide, and wherein said active composition is encapsulated in a coating, said coating comprising:
      (i) a physical barrier coating comprising gum arabic; and
      (ii) a reactive barrier coating comprising gum arabic and one or more phosphate salt,
      wherein said first reactive component is selected from the group consisting of acids, flavors, lecithin, peroxides, fluorides, water, aldehydes and glycerin;
      wherein said coating provides an interaction of the first reactive component and the one or more phosphate salt, wherein said interaction provides an increased shelf life of the tooth whitening gum composition of at least one year as measured by the presence of at least 75% of the peroxide remaining, or, provide a shelf-life of the tooth whitening gum composition of at least six months as measured by the presence of at least 90% of the peroxide remaining.

* * * * *